United States Patent [19]

Ujimoto et al.

[11] Patent Number: 4,943,340
[45] Date of Patent: Jul. 24, 1990

[54] APPARATUS FOR ATTACHING ELASTIC MEMBER TO WEARABLE ARTICLES

[75] Inventors: Hiroshi Ujimoto, Kawanoe; Hironori Nomura, Iyomishima; Toshinori Yamamoto, Kawanoe, all of Japan

[73] Assignee: Uni-Charm Corporation, Ehime, Japan

[21] Appl. No.: 297,587

[22] Filed: Jan. 12, 1989

[30] Foreign Application Priority Data

Jan. 14, 1988 [JP] Japan .................................. 63-7345

[51] Int. Cl.$^5$ ............................................. B32B 31/10
[52] U.S. Cl. .................................... 156/496; 156/164; 156/229; 156/519; 156/302
[58] Field of Search ............... 156/164, 494, 496, 229, 156/160, 265, 302, 303, 177, 439, 519, 552; 28/102; 26/88, 89

[56] References Cited

U.S. PATENT DOCUMENTS

| | | | |
|---|---|---|---|
| 2,429,177 | 10/1947 | Young | 156/164 |
| 2,434,111 | 1/1948 | Hawley, Jr. et al. | 156/164 |
| 2,728,941 | 1/1956 | Alles et al. | 26/89 X |
| 3,606,769 | 9/1971 | Walford | 28/102 X |
| 4,240,866 | 12/1980 | Rega | 156/496 |
| 4,284,454 | 8/1981 | Joa | 156/229 X |
| 4,285,747 | 8/1981 | Rega | 156/164 |
| 4,523,969 | 6/1985 | Spencer | 156/164 |
| 4,642,151 | 2/1987 | Coenen | 156/164 |
| 4,735,673 | 4/1988 | Piron | 156/496 |

Primary Examiner—Robert A. Dawson
Assistant Examiner—Michele K. Yoder
Attorney, Agent, or Firm—Robert W. J. Usher

[57] ABSTRACT

In the manufacture of disposable clothing such as diapers, elastic waistbands are attached to respective longitudinal ends of diapers while stretched in transversely extended condition. The diapers are arranged in end-to-end relation as a continuous of diaper precursors which is fed past a transfer station. A continuous sheet of elastic is coated on one side with adhesive except adjacent longitudinal edges thereof and the leading end is repeatedly severed transversely into successive individual elastic members which are then spaced apart and progressively stretched into extended condition while being fed one-by-one to the transfer station where the coated side is applied by a transfer drum to the web thereby transferring the elastic members at predetermined spacings to the web. The elastic members are then severed into two pieces while also severing through the web in a single cutting action to define adjacent ends of diapers with respective pieces of elastic members attached in extended condition.

4 Claims, 4 Drawing Sheets

APPARATUS FOR ATTACHING ELASTIC MEMBER TO WEARABLE ARTICLES

FIELD OF THE INVENTION

The invention relates to a method and an apparatus for attaching elastic members to disposable wearable articles, and more particularly concerns a method and an apparatus for attaching elastic members to disposable wearable articles such as a disposable diaper or training pants for babies.

BACKGROUND OF THE INVENTION

Various methods and apparatuses for attaching elastic members to leg-contacting portions of disposable wearable articles such as disposable diapers are known.

In the prior techniques, the articles are generally manufactured by a process which includes the steps of: feeding a continuous web which is a base material or precursor of an article along the manufacturing line, feeding a continuous elastic member to the continuous web while stretching the continuous elastic member to an extended condition in the feeding direction of the continuous web, attaching the elastic member in the extended condition to the continuous web with adhesive so that a layered continuous strip comprising the continuous elastic member and the continuous web is obtained, and severing the continuous strip at predetermined distances along transverse severance axes to obtain individual articles.

Methods and apparatuses for attaching elastic member to a waist band zone of disposable articles are also known. However, in those techniques, in contrast, generally, a continuous elastic member had to be stretched, not in the longitudinal feeding direction of the web, but in the transverse direction thereof and cut into the predetermined lengths when in the extended condition.

The respective individual elastic members obtained thereby were attached by adhesive to extend in the transverse direction of the continuous web.

However, difficulties have been encountered in handling the elastic members at the high speeds necessary for economic mass production and attaching them to the web which is also being fed at a high speed. An appropriate solution for such high speed handling has not yet been proposed.

OBJECTS OF THE INVENTION

An object of the invention is to provide a method and apparatus for effectively attaching at high speed an elastic member to a waist band zone of an article which is also handled at high speed and to a continuous web of base material or precursor of the article.

A further object of the invention is to provide an apparatus which is of relatively simple and inexpensive construction and yet which is reliable and can be readily assembled into an existing article production line to operate at the very high speeds necessary for more economic mass production.

SUMMARY OF THE INVENTION

According to one aspect of the invention, there is provided a method for attaching an elastic member to a wearable article, which method comprises the steps of feeding a continuous elastic sheet of predetermined width from a supply to a cutting station; coating an adhesive on one surface of the continuous elastic sheet except adjacent opposite longitudinal edge portions thereof during the feeding step; repeatedly cutting, at the cutting station, the continuous elastic sheet along a severance axis extending transversely thereof to form successive individual elastic members of predetermined lengths; feeding the individual elastic members so formed from the cutting station to a transfer station while spacing the elastic members a predetermined distance apart in the feeding direction thereof; stretching each elastic member to an extended condition in the transverse direction thereof; feeding a continuous web of article precursors in end-to-end relation past the transfer station; applying, at the transferring station, the coated side of each elastic member to the continuous web of article precursors at predetermined intervals in a longitudinal direction of the continuous web while maintaining each elastic member stretched in extended condition in the transverse direction of the continuous web during such application thereby to attach each elastic member to the continuous web; and, repeatedly severing the continuous web along a severance axis extending transversely of the feeding direction of the web to separate successive individual articles from the web.

Handling is thereby facilitated as only the individual elastic members are stretched, in contrast with the prior requirement to stretch continuously an elastic sheet of extended length.

Advantageously, each elastic member is progressively stretched in the transverse direction while being fed towards the transfer station thereby gradually increasing the transverse dimension of the elastic member during the feeding.

The progressive stretching of the individual elastic members gradually to increase their extended transverse length as they are fed towards the web of article precursors facilitates a smooth, continuous and stable operation with minimal vibration important for reliable operation of a continuous process running at high speed.

The severance axis passes through predetermined portions of the respective elastic members to separate each elastic member into two pieces in the feeding direction with the pieces on the respective adjacent ends of successive articles.

The step of severing the web to remove individual articles therefrom by severing on an axis through the elastic member results in a simplification in operation as only a single cut is required both to form a waistband at adjacent ends of successive articles and to separate the individual articles from the web.

According to another aspect of the invention, apparatus for attaching an elastic member to a wearable article comprises a cutting station; means for feeding a continuous elastic sheet of predetermined width from a supply to the cutting station and continuously applying an adhesive coating on one surface of the elastic sheet except adjacent longitudinal edge portions thereof; cutting means at the cutting station for successively forming individual elastic members by repeatedly cutting the continuous elastic sheet along a severance axis extending in a transverse direction thereof; transfer means; feed means extending from the cutting station to the transfer means for feeding the successively formed elastic members from the cutting means to the transfer means while spacing the elastic members a predetermined distance apart in the feeding direction thereof; means for stretching each elastic member to an extended condition in the transverse direction; means for feeding a continuous web of article precursors in end-to-end relation past the transfer means; the transfer means being arranged to apply the coated surface of each elastic member to the continuous web of article precursors at predetermined intervals in a longitudinal direction of the continuous web during the feeding of the web while maintaining the elastic member stretched in extended condition in the transverse direction of the continuous web thereby to attach each elastic member to the continuous web; and, means for repeatedly severing the continuous web along a severance axis extending transversely of the web to separate successive individual articles from the web.

The means for severing the continuous web is advantageously mounted so that the severance axis extends through a predetermined portion of the successive respective elastic members thereby to separate each elastic member into two pieces in the feeding direction of the continuous web, which pieces are on respective adjacent ends of successive individual articles.

The feeding, spacing and stretching means preferably comprises first and second elastic member gripping means arranged to grip respective opposite transverse ends of the successive individual elastic members; means moving respective gripping means along divergent feed paths extending from the severing means to the transfer means thereby progressively to stretch the elastic members in the transverse direction during such feeding movement to increase gradually the transverse dimensions of the elastic members.

More specifically, the feeding, spacing and stretching means may comprise first and second pairs of rollers; first and second pairs of endless belts mounted around the respective pairs of rollers for driven movement thereby; the rollers of each pair being spaced apart in the feed direction and located adjacent the severing means and the transfer means respectively; means on the rollers to maintain the belts of each pair extending spaced apart in divergent relation as they extend in the feed direction from the severing means to the transfer means with the belts of the first pair diverging at the same angle as the belts of the second pair; the first and second pairs of rollers being driven respectively in opposite rotational senses and arranged with respective forwardly driven portions of the belts of the first pair of belts extending in the feed direction aligned with and adjacent forwardly driven portions of the respective belts of the second pair so that respective belts of the first pair cooperate with respective belts of the second pair to grip between them the ends of the elastic members thereby to feed successive elastic members from the cutting station to the transfer station while progressively stretching the elastic members in the transverse direction during such feeding movement. The stretching and feeding apparatus is of relatively simple construction with minimum vibration requiring substantially no reciprocating parts, and can readily be assembled to or integrated with an article production line.

BRIEF DESCRIPTION OF THE DRAWINGS

An example of apparatus for performing the method according to the invention is shown in the accompanying drawings in which.

DESCRIPTION OF SPECIFIC EXAMPLE

Figure 1:
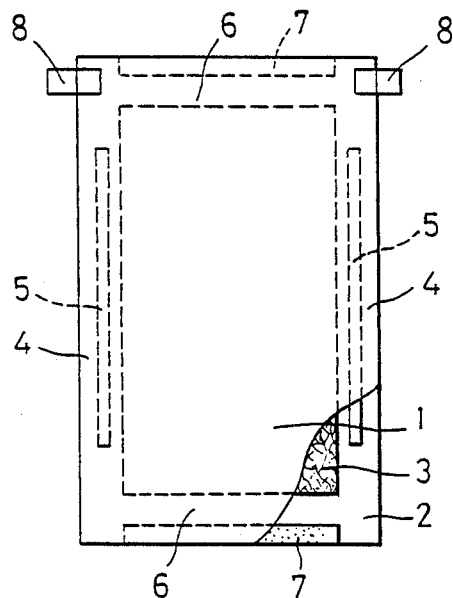
FIG. 1 is a plan view partially broken away of a disposable diaper, an example of a wearable article manufactured by the method and apparatus according to the invention.

As shown in FIG. 1, a disposable diaper comprises a moisture pervious topsheet 1, a moisture impervious backsheet 2 and an absorbent core 3 interposed between both sheets. Elastic members 5 for leg-contacting are secured by adhesive in side flaps 4 which extend longitudinally of the diaper while being stretched in extended condition in the longitudinal direction of the diaper. Each longitudinally extending side-flap 4 is defined by overlapping edge portions of both sheets 1 and 2 which extend laterally beyond longitudinal edges of the absorbent core 3. Elastic members 7, forming waistbands, are secured by adhesive into laterally extending flap 6 while being stretched in extended condition in the transverse direction, each lateral end flap being formed by overlapping portions of the sheets 1 and 2 which extend longitudinally of the diaper beyond the lateral edges of the absorbent core. Tape fasteners 8 are provided on the backsheet at the intersections of one laterally extending end flap and the longitudinally extending side flaps.

Figure 2:
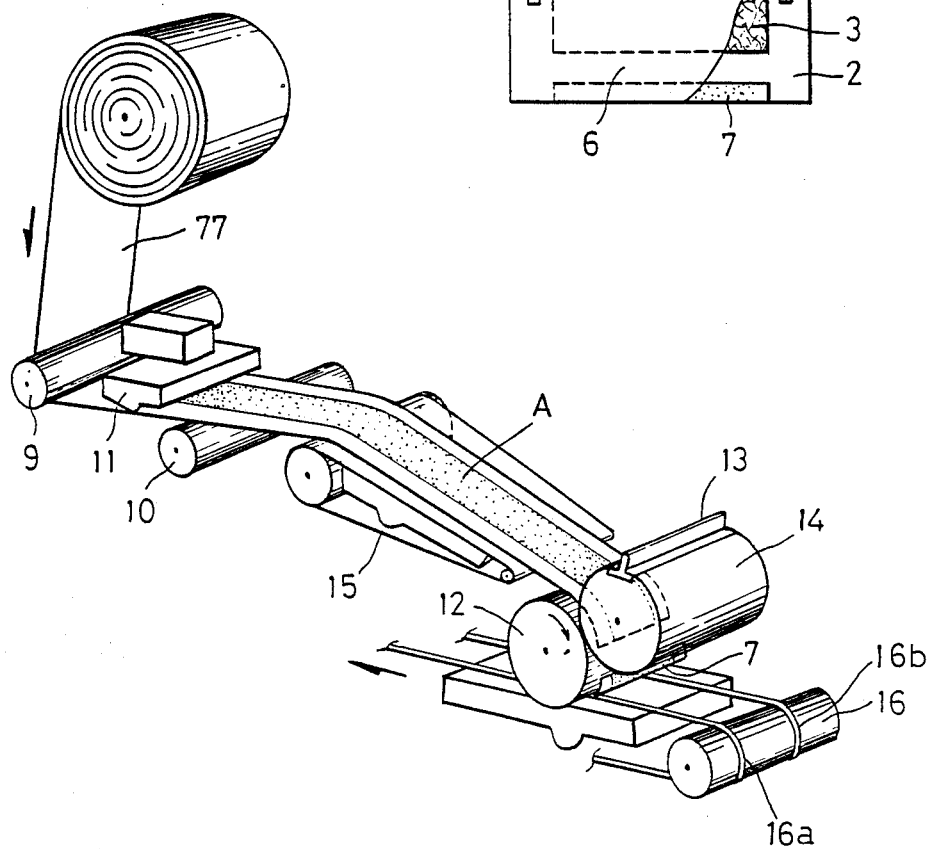
FIG. 2 is a perspective view of a part of the apparatus incorporating means for applying an adhesive to a continuous elastic sheet and for severing the elastic sheet to provide successive individual elastic members.

As shown in FIG. 2, a supply roll carries a continuous elastic sheet 77 of predetermined width and which is preferably made of a polyurethane foam. The continuous elastic sheet is drawn in a longitudinal feed direction, through and between a pair of nip rollers 12 and 14, nip roller 14 having a cutting knife 13 incorporated thereon, while an adhesive applicator 11 is provided to apply hot-melt adhesive A to one surface of the continuous elastic sheet with the exception of those portions of the surface adjacent the longitudinally extending edge portions. The adhesive coating A may be applied in a continuous, intermittent or dotted form.

During its passage between the pair of nip rollers 12 and 14, the leading end of the elastic sheet 77 is repeatedly cut along a severance line extending in a direction transverse of the feed direction by the knife 13 forming successive individual elastic members elongate in the transverse direction and of predetermined lengths. The peripheral surface of the roller 14 is coated with silicon resin to prevent adhesive 8 from clinging thereto. A suction device 15 is disposed between the roller 10 and the pair of rollers 12, 14 to prevent wandering or meandering of the elastic sheet 77, and provides sufficient force to hold the elastic sheet while permitting the elastic sheet to be fed.

Figure 3:
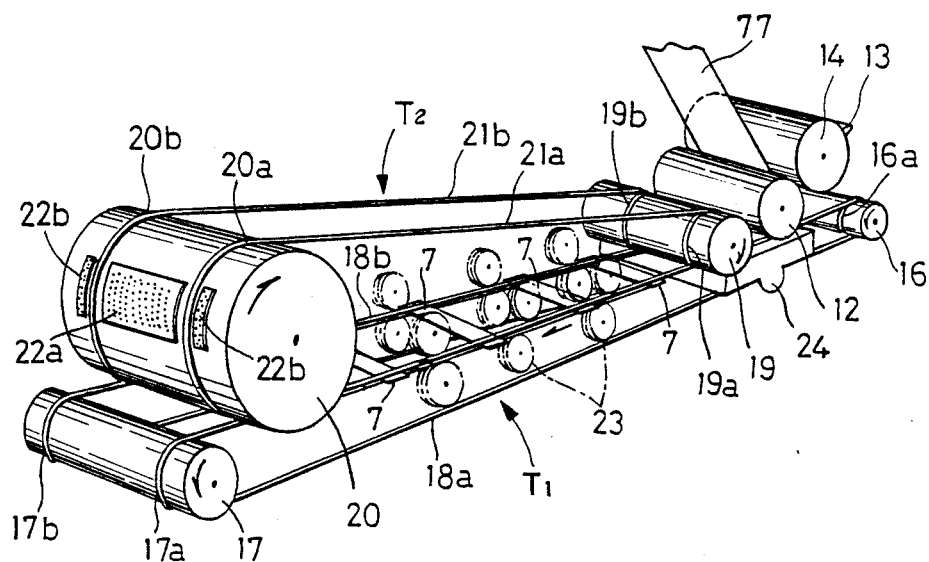
FIG. 3 is a perspective view of a part of the apparatus for stretching and transferring said individual elastic members.
Figure 4:
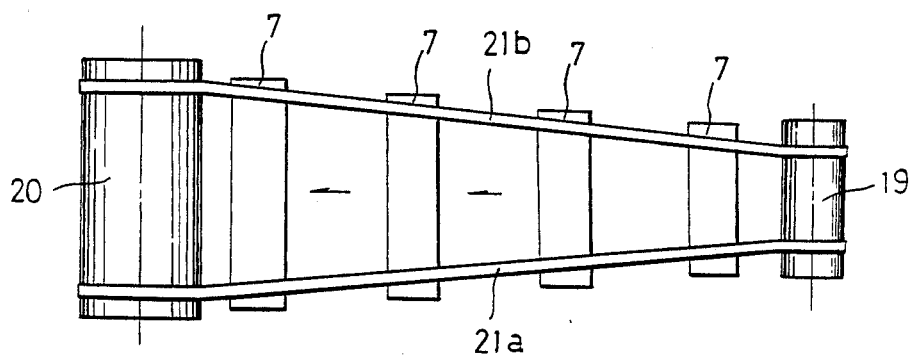
FIG. 4 is a schematic top plan view showing an upper part of the portion of apparatus shown in FIG. 3.

A pair of stretching and feeding devices T1, T2 are arranged downstream of the rollers 12, 14 as shown in FIG. 3. The device T1 has a linear velocity which is the same as that of the device T2 but higher than the circumferential linear velocity of the rollers 12, 14. The device T1 includes a driven roller 16 disposed in close proximity to the rollers 12, 14, a driving roller 17 located downstream of the driven roller 16, and belts 18A, 18B mounted around the rollers 16 and 17. The belts 18A, 18B each have a V-shaped cross-section and engage V-shaped groove 16A, 16B and 17A, 17B extending around the circumference of the rollers 16 and 17, respectively.

The V-shaped grooves of both rollers 16 and 17 are formed on their respective circumferentially extending surfaces at locations adjacent their side edges and the spacing between the grooves 17A and 17B is greater than that between grooves 16A and 16B so that the distance between the belts 18A, 18B progressively increases as they extend from roller 16 to roller 17. The device T2 is disposed on an upper surface or side defined by the device T1 and comprises a driven roller 19 arranged downstream both of the roller 16 and the nip rollers 12 and 14, a drum-shaped driving roller 20 located downstream of the roller 19 and upstream of the roller 17, and belts 21A and 21B mounted around the rollers 19 and 20. The belts 21A and 21B each also have a V-shaped cross-section which is similar to that of the belts 18A and 18B and engage V-shaped grooves 19A, 19B and 20A, 20B formed on the respective circumferentially extending surfaces adjacent the side edges of the rollers 19 and 20 respectively. The distance between the grooves 19A, 19B is less than that between the grooves 20A, 20B so that the belts 21A, 21B progressively diverge as they extend from the roller 19 to the roller 20 and the relative separations of the grooves 19A, 19B and 20A, 20B is chosen so that the belts 21A, 21B diverge at the same angle as belts 18A, 18B to lie adjacent belts 18A, 18B throughout their length in the feed direction. A pair of suction devices are provided inside the roller 20 (not shown) and have active ducts 22A, 22B exposed at opposed portions of the circumferential surface of the roller 20. The suction duct 22A is located between the grooves 20A, 20B and the suction ducts 22B are arranged at opposite sides of the suction surface 22A outside the grooves 21A, 21B. Drum rollers having such suction devices are well known and thus further details thereof are not included herein. A plurality of guide rollers 23 each having a V-shaped groove are arranged between forward and return portions of belts 18A, 18B and adjacent and above the forward portion of belts 21A, 21B at predetermined locations in their direction of movement to ensure stable running of the belts in gripping engagement with the elastic members while maintaining a predetermined clearance therebetween.

A suction device 24 is disposed underneath an area where the individual elastic members 7 severed from the strip exit and are withdrawn from the nip rollers 12, 14, such suction device providing a suction force sufficient to hold an individual elastic member while permitting the elastic member when gripped by the belts 18A, 18B and the belts 21A, 21B to be fed.

The suction device 24 locates the elastic member on a forwardly running portion of the moving belts 18A, 18B and, immediately thereafter, as a result of the forward movement of the belts, the transverse end portions of the elastic member 7 corresponding to the longitudinal edge portions of the continuous sheet on which adhesive A is not applied, is trapped between the belts 18A, 18B and belts 21A, 21B respectively to be gripped and fed thereby. At this time, the preceding elastic member 7 has been spaced apart from a subsequent elastic member 7 in the feed direction by a predetermined amount as the belts 18A, 18B, 21A, 21B have a higher linear velocity than the circumferential linear velocity of the nip rollers 12, 14. The spacing of successive elastic members corresponds to the spacing required to obtain synchronous registration of successive members with the suction ducts 22A, 22B of the rotating roller 20. As a result of the divergence of the belts in the feed direction, successive elastic members are stretched in the transverse direction to an extended condition of predetermined transverse dimension during their travel to roller 20. The extended elastic members synchronously register with the suction ducts 22A, 22B of the rotating roller 20 such that a central portion of an uncoated surface of each member faces, and is held by, the suction duct 22A, while uncoated side edges are held by suction ducts 22B.

Figure 5:
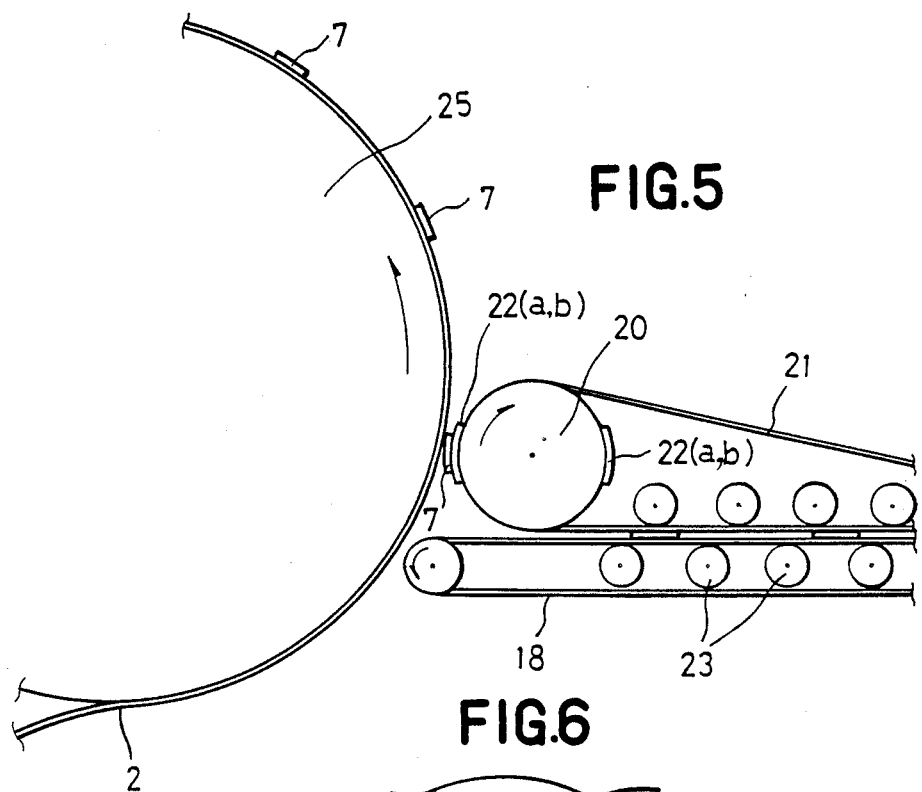
FIG. 5 is a side elevation showing, schematically, a portion of the apparatus adhesively securing successive elastic members to a continuous web of article precursors wound around a drum.
Figure 6:
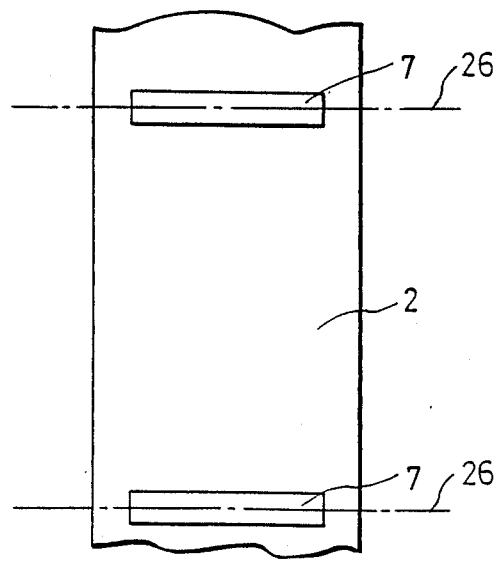
FIG. 6 is a plan view of the web carrying the elastic members.

As shown in FIG. 5, a drum-shaped roller 25 having a continuous web defining backsheet 2, (or the precursor of the articles), extending around its circumferential surface is mounted adjacent and in opposed relation to the circumferential surface of the roller 20 so that adhesive coated surfaces of successive elastic members held on the suction ducts 22A, 22B contact, adhere to and are thereby transferred to the backsheet, at which instant the suction action of the suction ducts 22A, 22B holding the elastic member is stopped. As a result, as shown in FIGS. 5 and 6, the elastic members are adhesively attached to the backsheet 2 on the roller at predetermined intervals around its circumference, that is, in the longitudinal (feeding) direction of the backsheet while being stretched in extended condition in the transverse direction thereof.

It should be noted that the interval or spacing between the elastic members transferred to the web can be altered by adjusting the relative circumferential linear velocities of the roller 20 and the roller 25.

Figure 7:
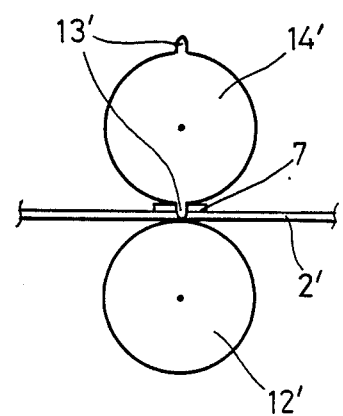
FIG. 7 is a side elevation of a suitable web severing device of known type.

Although not shown in the drawings, the backsheet 2 includes other article members such as said continuous topsheet, said core interposed between the backing and topsheets, and said longitudinally extending or continuous elastic members, thereby forming a continuous strip of individual articles in end-to-end relation. The continuous strip is then severed along a severance axis extending transversely through the center of successive respective elastic members by operation of the severing nip shown in FIG. 7, which is similar in design to that shown in FIG. 2, and is mounted downstream of the roller 25, both separating the individual articles from the strip and providing portions of the bisected elastic member simultaneously at waistband portions of adjacent articles by only a single cutting stroke.

Although, in this embodiment of the invention, the elastic members are applied to the backsheet, it is obvious that the elastic member can be applied to a continuous web defining the topsheet.

In the above described example of a method and apparatus for attaching an elastic member to a wearable article, individual elastic members are obtained by repeatedly cutting the leading end of a continuous elastic sheet in the transverse direction after an adhesive coating is applied thereto and the individual elastic members are stretched to predetermined extended lengths in the transverse direction and attached to a continuous web constituting a part or a precursor of the wearable articles at a predetermined intervals along the web. Thus the production line for the continuous elastic sheet and individual elastic members can be arranged on the same line which produces the other members constituting the article, enabling a relative increase in speed of both production lines so that articles having elastic members which extend at right angles to the longitudinal dimensions of the articles can be manufactured at a lower cost.

In addition, only a single cut is necessary both to divide the elastic members to form two waistband portions, one on each of adjacent ends of respective articles and to separate successive articles from the continuous web.

The apparatus according is of relatively simple construction and can be easily assembled to the article manufacturing line.

What is claimed is:

1. An apparatus for attaching an elastic member to a wearable article, which apparatus comprises:
   a cutting station;
   means for feeding a continuous elastic sheet of predetermined width from a supply to the cutting station and continuously applying an adhesive coating on one surface of the elastic sheet except adjacent longitudinal edge portions thereof;
   cutting means at the cutting station for successively forming individual elastic members by repeatedly cutting the continuous elastic sheet along a severance axis extending in a transverse direction thereof;
   transfer means for the elastic members;
   feeding, spacing and stretching means for feeding the successively formed elastic members from the cutting means to the transfer means while spacing the elastic members a predetermined distance apart in the feeding direction thereof and stretching each elastic member to an extended condition in the transverse direction comprising:
   first and second pairs of rollers;
   first and second pairs of endless belts mounted around the respective pairs of rollers for driven movement thereby;
   the rollers of each pair being spaced apart in the feed direction and located adjacent the cutting means and the transfer means respectively;
   means on the rollers to maintain the belts of each pair extending spaced apart in divergent relation as they extend in the feed direction from the cutting means to the transfer means with the belts of the first pair diverging at the same angle as the belts of the second pair;
   the first and second pairs of rollers being driven respectively in opposite rotational senses and arranged with respective forwardly driven portions of the belts of the first pair of belts extending in the feed direction aligned with and adjacent forwardly driven portions of the respective belts of the second pair so that respective belts of the first pair cooperate with respective belts of the second pair to grip between them the ends of the elastic members thereby to feed successive elastic members from the cutting station to the transfer means while progressively stretching the elastic members in the transverse direction during such feeding movement;
   means for feeding a continuous web of article precursors in end-to-end relation past the transfer means;
   the transfer means comprising:
   a roller of the second pair of rollers, which roller is located adjacent the continuous web of article precursors and includes means to receive elastic members released from the belts and releasably to hold such elastic members in extended condition transversely of the continuous web of article precursors and to press the coated surfaces of the elastic members so held successively against the web at predetermined intervals in a longitudinal direction of the continuous web during the feeding of the web thereby to transfer and to attach each elastic member to the continuous web; and,
   means for repeatedly severing the continuous web along a severance axis extending transversely of the web to separate successive individual articles from the web.

2. Apparatus according to claim 1 in which the means for cutting the continuous web is mounted so that the severance axis extends through a predetermined portion of the successive respective elastic members thereby to separate each elastic member into two pieces in the feeding direction of the continuous web, which pieces are on respective adjacent ends of successive individual articles.

3. Apparatus according to claim 1 in which the web feeding means comprises a rotating drum around which the web extends.

4. Apparatus according to claim 2 in which the web feeding means comprises a rotating drum around which the web extends.

* * * * *